United States Patent [19]
Fortin

[11] Patent Number: 5,429,505
[45] Date of Patent: Jul. 4, 1995

[54] TEETH PROSTHESIS AND METHOD FOR MOUNTING AND REMOVING A SUPRASTRUCTURE THEREOF

[75] Inventor: Yvan Fortin, St-Raymond de Portneuf, Canada

[73] Assignee: Clinique Dentaire Fortin Et Vallee Inc., Comte Portneuf, Canada

[21] Appl. No.: 193,426

[22] Filed: Feb. 8, 1994

[51] Int. Cl.[6] ............................................. A61C 13/12
[52] U.S. Cl. .................................. 433/172; 433/173
[58] Field of Search ............... 433/172, 173, 193, 195

[56] References Cited

U.S. PATENT DOCUMENTS

| | | | |
|---|---|---|---|
| 2,644,231 | 7/1953 | Brennan | 433/173 |
| 3,748,739 | 7/1973 | Thibert | 433/173 |
| 4,085,506 | 4/1978 | Lew | 433/173 |
| 4,904,186 | 2/1990 | Mays | 433/172 |
| 4,931,016 | 6/1990 | Sillard | 433/172 |
| 5,234,341 | 8/1993 | Johansen | 433/173 |

FOREIGN PATENT DOCUMENTS 1340429  9/1963  France ................ 433/172

OTHER PUBLICATIONS

"Removable Closure of the Interdental Space (C.I.S.)", Arnold A. Gaerny, Translated from the revised and enlarged German edition by Thomas M. Hassell, D.D.S., Zurich, Switzerland, Published in Berlin and Chicago, 1972.
Advertising document entitled "Spark Erosion System" from Dental Arts Laboratories Inc. (No date).
"*Prothese Dentaire*", No. 52, Feb. 1991, pp. 27-38 MK1 Fastener, Polydental Laboratory, Brussels, Belgium.

Primary Examiner—Cary E. O'Connor
Attorney, Agent, or Firm—Merchant & Gould Smith, Edell, Welter & Schmidt

[57] ABSTRACT

A teeth prosthesis for an upper maxilla includes an infrastructure, a suprastructure, and an assembly for a removable attachment of the suprastructure with the infrastructure. The infrastructure includes at least three implants, one connection bar, and an assembly for removably fastening the connection bar with and against each head of the implants. The suprastructure includes a first member made of cast metal or alloy having an intrados provided with an opening giving access to a housing of such size and depth to allow the housing of the connection bar therein, a second member immovably attached with the first member, and a set of teeth immovably attached with the first member and the second member. The assembly includes two first fastening members, and a second fastening member.

10 Claims, 3 Drawing Sheets

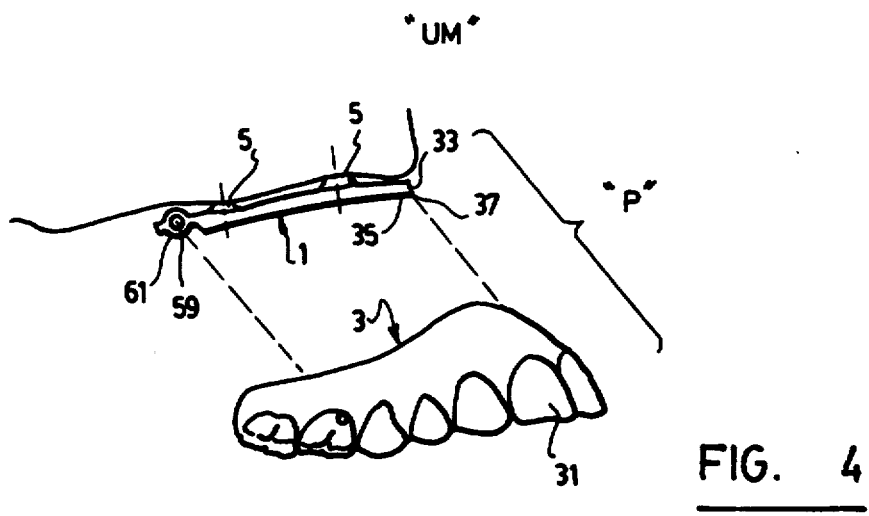
FIG. 4
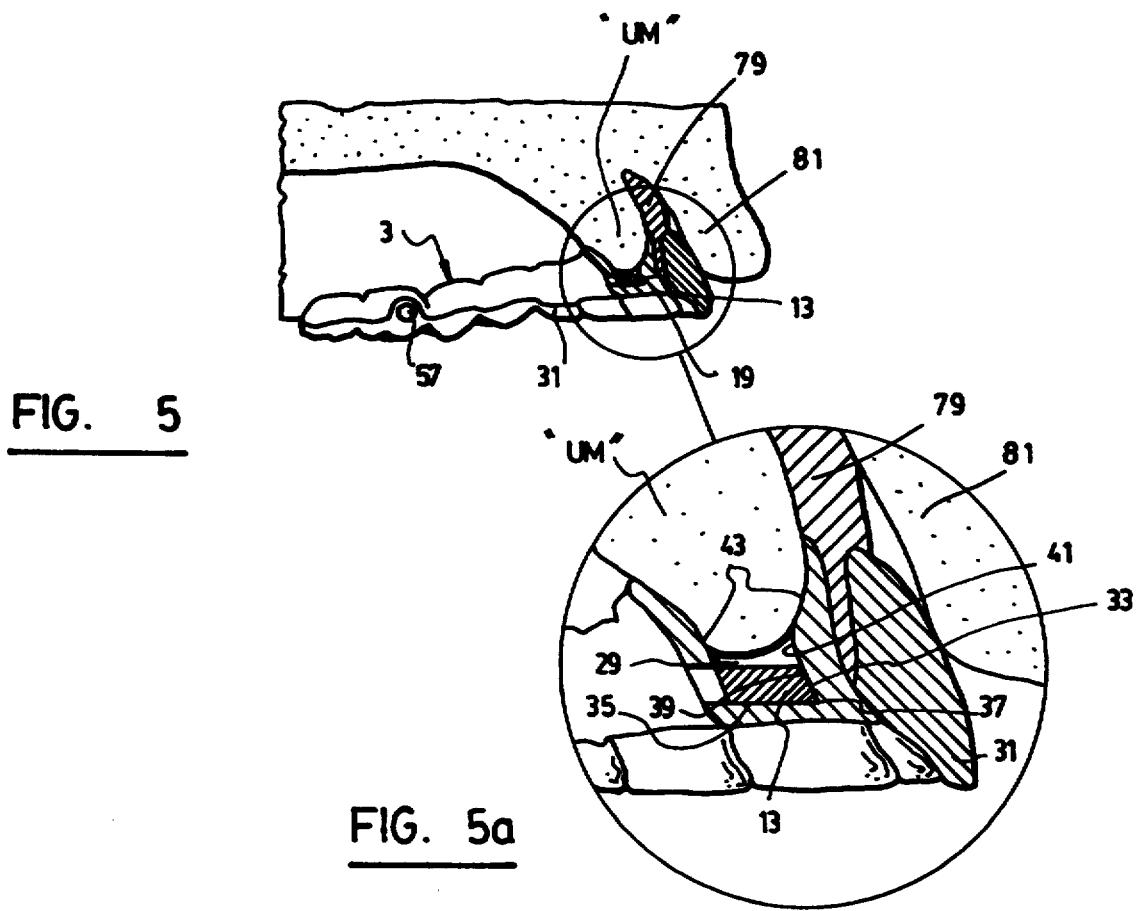
FIG. 5
FIG. 5a

TEETH PROSTHESIS AND METHOD FOR MOUNTING AND REMOVING A SUPRASTRUCTURE THEREOF

BACKGROUND OF THE INVENTION

1. Field of the Invention

The present invention relates to an improved teeth prosthesis for an upper maxilla and to a method for mounting or removing a suprastructure of said prosthesis on or from a fixed infrastructure.

2. Brief Description of the Prior Art

It is known in the art to embody teeth prosthesis for a lower maxilla, said teeth prosthesis being of the type comprising an infrastructure, a suprastructure and means for a removable attachment of the suprastructure with the infrastructure.

The infrastructure comprises:
- at least two implants, advantageously at least 3 and preferably four to six, each implant having opposite ends, one end of each implant being anchored in the bone of the lower maxilla while the opposite end is sticking out of the gingiva and defines a head to said implant,
- one connection bar having a fore part and two opposite rear ends, said connection bar being shaped and sized to be substantially facing the gingiva of the lower maxilla, and
- means for removably fastening the connection bar with and against each head of said implants.

The suprastructure comprises:
- a member made of cast metal or alloy, said member having a fore part and two rear ends, said member having an intrados provided with an opening giving access to a housing provided in the member, said housing being of such size and depth to allow the connection bar to be housed therein,
- a saddle immovably attached with the member, and
- a set of teeth immovably attached with the member and the saddle.

The means for a removable attachment of the suprastructure with the infrastructure comprises fastening means that are respectively immovably attached with a corresponding rear end of the member, for removably attaching them with corresponding ends of the connection bar. Preferably such fastening means comprises:
- a device comprising a sleeve, especially a cylindrical sleeve, immovably attached with a corresponding end of the member, said cylindrical sleeve being provided with a lateral opening, and a pin slidably mounted inside the sleeve and movable between two distinct positions, a first distinct position being defined when the pin is not facing the lateral opening and a second distinct position being defined when the pin is facing the lateral opening,
- a bore provided in a protouberance, especially a small protuberance, near a corresponding end of the connection bar, said protuberance being shaped and sized to be housed in a corresponding cylindrical sleeve through the lateral opening of said cylindrical sleeve, to be co-axial with a longitudinal axis of the cylindrical sleeve and to be removably engaged by the pin.

Advantageously, each of aforesaid fastening means are of the type of those sold under the trade mark MK1 (Polydental Laboratory, BELGIUM).

However, even though aforesaid prior art teeth prothesis can work correctly when installed on the lower maxilla, it become unusable for the upper maxilla because it was not possible to prevent the fore part (i.e. the anterior part) of the suprastructure to separate from the infrastructure without having to negatively affect the esthetic appearance of the fore part of said prosthesis. In fact there is generally not enough space to provide a conventional lock at the anterior part.

Therefore, there was a very strong need for a way allowing to efficiently fasten the fore part of a suprastructure of a teeth prosthesis for an upper maxilla, comprising a fixed infrastructure and a removable suprastructure, without affecting the esthetic characteristic of the fore part of said suprastructure.

Also, there was a strong need to obtain a simple and easy method for mounting and removing a superstructure of a teeth prosthesis for an upper maxilla. Indeed, methods actually known for mounting and removing a suprastructure on or from an fixed infrastructure are laborious.

SUMMARY OF THE INVENTION

A first object of the present invention is to provide a teeth prosthesis that can be easily, efficiently and safely installed on the upper maxilla, said prosthesis having a fixed infrastructure and a removable suprastructure that can be easily mounted on the infrastructure or removed from said infrastructure.

Another object of the present invention is to provide a teeth prosthesis where the fore part of the suprastructure can not separate from the fore part of the infrastructure when the rear ends of the suprastructure are attached with corresponding ends of a connection bar which is part of the infrastructure.

Another object of the present invention is to provide a teeth prosthesis where the person wearing it can has the feeling of having its own original teeth of the upper maxilla.

Another object of the present invention is to provide a teeth prosthesis which is further provided on its suprastructure, with means allowing to support the upper lip and then prevent any disformation of the same.

Another object of the present invention is to provide a teeth prosthesis where the person wearing it can easily remove the suprastructure for cleaning and hygiene purposes and then easily remount said suprastructure.

Another object of the present invention is to provide a method for easily mounting or removing the suprastructure of a teeth prosthesis defined hereinbefore as being part of the invention.

Another object of the present invention is to provide a teeth prosthesis for an upper maxilla that works exactly as a fixe bridge and has at once the same advantages of a fixe bridge and all the advantages of a removable bridge.

More particularly, the invention relates to a teeth prosthesis for an upper maxilla, said prosthesis comprising a fixed infrastructure, a suprastructure and means for a removable attachment of the suprastructure with the infrastructure;

said infrastructure comprising:
- at least three implants, preferably at least four, each implant having opposite ends, one end of each implant being anchored in the bone of the upper maxilla while the opposite end is sticking out of the gingiva and defines a head to said implant,
- one connection bar having a fore part and two opposite rear ends, said bar being shaped and sized to be substantially facing the gingiva of the upper maxilla, means for removably fastening the connection bar with and against each head of said implants;

said suprastructure comprising:

a first member made of cast metal or alloy, having a fore part and two rear ends and having an intrados provided with an opening giving access to a housing of such size and depth to allow the connection bar to be housed therein;

a second member immovably attached with the first member, said first and second members defining together a saddle;

a set of teeth immovably attached with the first member and the second member;

said means for a removable attachment of the suprastructure with the infrastructure comprising:

two first fastening means that are respectively immovably attached with a corresponding rear end of the first member for removably attaching them with corresponding ends of the connection bar, a second fastening means comprising a first sliding face provided on the fore part of the connection bar and inclined toward the rear of said connection bar, a lower part of said face forming with a bottom face of said connection bar an edge projecting ahead the connection bar, and a second sliding face provided on a fore wall of the housing of the first member, said sliding faces, when the first and second fastening means are attached with the connection bar, cooperating together to lock the fore wall of the housing of the first member against the fore part of the connection bar and press a fore part of the saddle against the corresponding portion of gingiva of the upper maxilla.

The invention also relates to a method of use of a teeth prosthesis as defined hereinbefore, wherein:

for mounting the suprastructure on the infrastructure, one only have to house both sliding surface one against the other and to fasten the rear ends of the first member with the corresponding rear ends of the connection bar;

for removing the suprastructure from the infrastructure, one only have to unfasten the rear ends of the first member from the corresponding rear ends of the connection bar and to move the sliding faces away from each other.

BRIEF DESCRIPTION OF THE DRAWINGS

The invention will be better understood with reference to the following non-restrictive description of preferred embodiments thereof, taken in connection with the accompanying drawings.

FIG. 4 is an exploded side elevational view of the suprastructure and the infrastructure of a teeth prosthesis according to the invention with a partial illustration of the upper maxilla;

FIG. 5 is a longitudinal cross-sectional view of a teeth prosthesis according to the invention with a partial illustration of the upper maxilla and of the upper lip;

FIG. 5a is an enlarge view of a part of FIG. 5;

DESCRIPTION OF PREFERRED EMBODIMENTS

Figure 1:
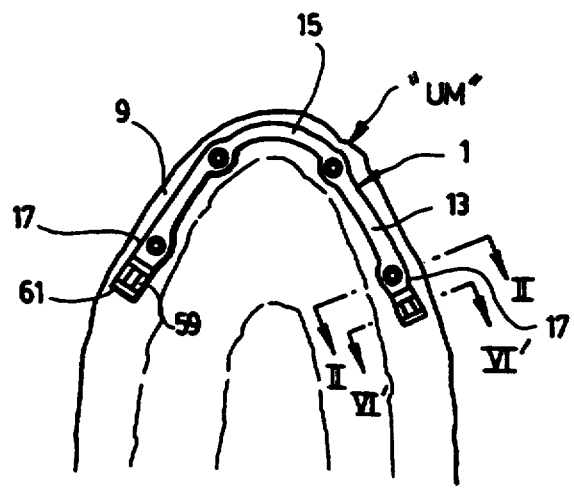
FIG. 1 is a bottom plan view of the infrastructure of a teeth prosthesis according to the invention with a partial view of the upper maxilla.
Figure 2:
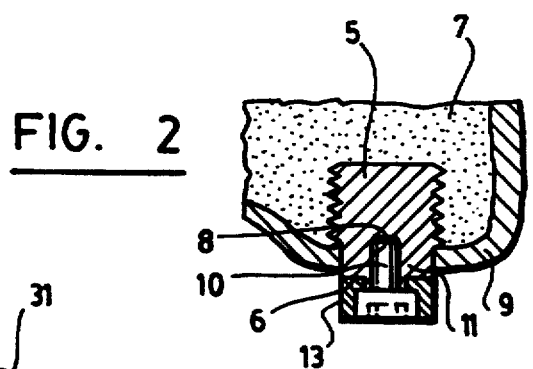
FIG. 2 is a cross sectional view according to line II—II in FIG. 1.
Figure 3:
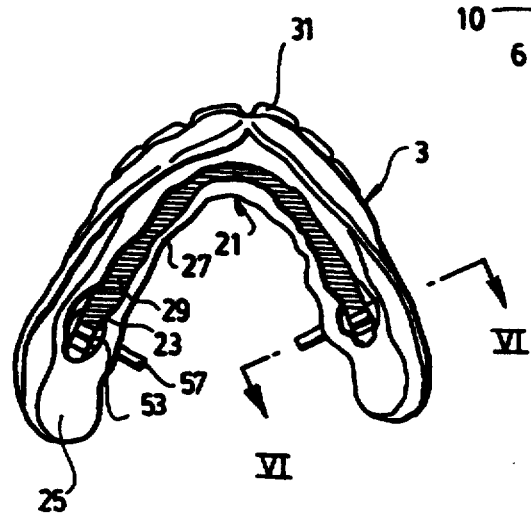
FIG. 3 is a top plan view of the suprastructure of a teeth prosthesis according to the invention with a pin in open position.
Figure 6:
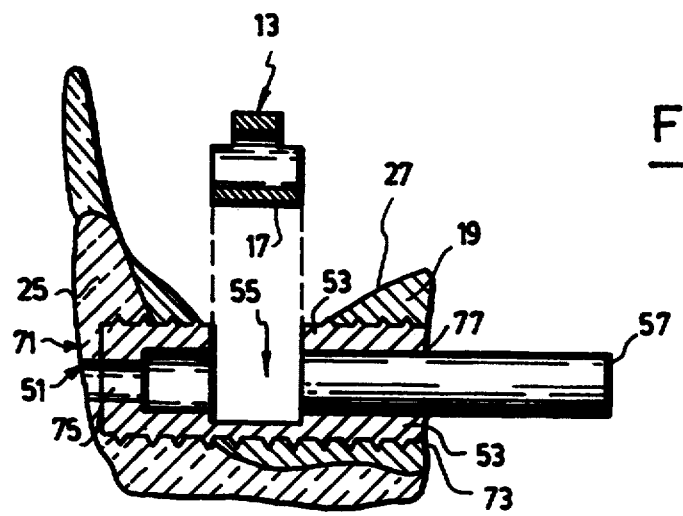
FIG. 6 is a cross-sectional view according to line VI—VI in FIG. 3 and line VI'—VI' of FIG. 1 with the pin in open position and the protuberance of the connection bar removed from the member.
Figure 7:
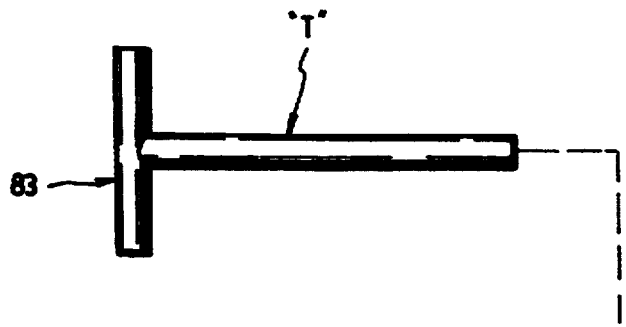
FIG. 7 is a cross-sectional view similar to the one of FIG. 6 except the protuberance of the connection bar of the infrastructure is aligned with the sleeve of the suprastructure.
Figure 7:
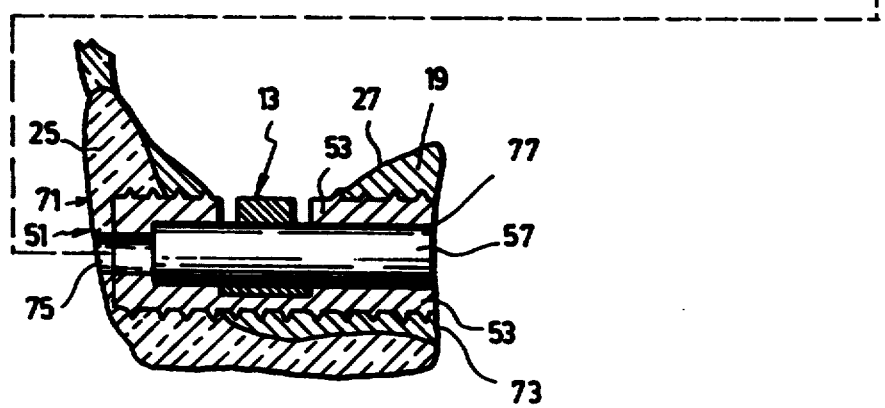

Referring to FIGS. 1 to 7, the invention relates to a teeth prosthesis "P" for an upper maxilla "UM", said prosthesis "P" comprising an infrastructure 1, a suprastructure 3 and means for a removable attachment of the suprastructure 3 with the infrastructure 1.

The infrastructure 1 comprises:

at least three implants 5, preferably four as illustrated, and more preferably 5 or 6 implants, each implant 5 having opposite ends, one end of each implant being anchored in the bone 7 of the upper maxilla "UM" while the opposite end is sticking out of the gingiva 9 defines a head 11 to said implant 5;

one connection bar 13 having a fore part 15 and two opposite rear ends 17, said connection bar 13 being shaped and sized to be substantially facing the gingiva 9 of the upper maxilla "UM"; and means for removably fastening the connection bar 13 with and against each head 11 of said implants 5.

Each implant 5 may be of the type of those well known and recognized in the art and anchored in the bone of the upper maxilla according to technics well known to man skilled in the art. Said implant may be made of titanium.

The connection bar 13 is built in laboratory by waxing technique (i.e. thus custom made), except the fore part of said connection bar which is milled to define the inclined sliding face 33 and the edge 37. The milling of the connector bar 13 is achieved with a milling machine commonly used by dental laboratory and using usual drills and/or cutters. The technic for modelling the shape of a connection bar 13 with a milling machine is well known in the art and does not need to be explained in detail.

Preferably, each implant 5 may be further provided, as means for fastening the connection bar 13 with and against each head 11, with a shoulder 6 and a central threaded bore 8, the connection bar 13 being provided, of said implants, with an opening corresponding to a head 11, and for each implants a threaded screw 10 engaging the threaded bore 8 to press the connection bar 13 against the shoulder 6 and locked said connection bar on said head 11. Advantageously, as illustrated, the connection bar 13 is at a small distance from the gingiva 9. Optionally, a spacing member (not shown) may be positioned between the head 11 and the connection bar 13, especially to adjust by distance between the gingiva 9 and said bar 13.

The suprastructure 3 comprises:

a first member 19 made of cast metal or alloy, and having a fore part 21 and two rear ends 23, having an intrados 27 provided with an opening giving access to a housing 29 provided in the member 19, said housing 29 being of such size and depth to allow the housing of the connection bar 13 to be housed therein, a second member 25 immovably attached with the first member 19, said members 19 and 25 defining together a saddle, and a set of teeth 31 immovably attached with the first member 19 and the member 25.

The means for a removable attachment of the suprastructure 3 with the infrastructure 1 comprises:

two first fastening means that are respectively immovably attached with a corresponding rear end 23 of the first member for removably attaching them with corresponding ends 17 of the connection bar 13, a second fastening means comprising a first sliding face 33 provided on the fore part 15 of the connection bar 13 and inclined toward the rear of said connection bar 13, a lower part of said face forming with a bottom face 35 of said connection bar 13 an edge 37 projecting ahead the connection bar 13, and a second sliding face 39 provided on a fore wall 41 of the housing 29 of the first member 19, said sliding faces 33 and 39, when the first and second fastening means are attached with the connection bar 13, cooperating together to lock the fore part 41 of the first member 19 against the fore part 15 of the connection bar 13 and press a fore part 43 of the suprastructure against the corresponding portion of gingiva 9 of the upper maxilla "UM".

More particularly each first fastening means respectively comprises:

a device 51 that is immovably attached with a corresponding end of the member 19, said device 51 comprising a cylindrical sleeve 53 provided with a lateral opening 55, and a pin 57 slidably mounted inside the sleeve 53 and movable between two distinct positions, a first distinct position being defined when the pin 57 is not facing the lateral opening 53 and a second distinct position being defined when the pin 57 is facing the lateral opening 53, a bore 59 provided in a small protuberance 61 near corresponding end 17 of the connection bar 13, said protuberance 61 being shaped and sized to be housed in a corresponding cylindrical sleeve 53 through the lateral opening 55 of said cylindrical sleeve 53 and co-axial with a longitudinal axis of the cylindrical sleeve 53. The bore 59 is sized to be removably engaged by the pin 57.

Preferably, each cylindrical sleeve 53 and the pin 57 are both of such size to be completely housed between an inner and an outer lateral walls 71, 73 of the suprastructure 3, when the pin 57 is slid completely inside the cylindrical sleeve 53, and wherein a portion of the pin 57 projects from the corresponding inner wall 71 of the suprastructure 3 when the pin 57 is slid to be not facing the lateral opening 55 of the cylindrical sleeve 53, a first bore 75 co-axial with the longitudinal axis of the pin 57 being provided in the corresponding inner wall 71 of the suprastructure 3 to allow the passage of the pin 57 therethrough and a second bore 77 of size smaller than a diameter of the pin 57 and co-axial with the longitudinal axis of said pin 57 being provided in the corresponding outer wall 73 of the suprastructure 3, said second bore 77 allowing a small tool "T" to push the pin 57 from a distinct position where it faces the lateral opening 55 of the cylindrical sleeve 53 toward the other distinct position where said pin 57 does not face said lateral opening 55.

Advantageously, the metal or alloy used to form the first member 19 may be one of those well known in dentistry, especially gold or gold alloys on palladium or palladium alloys.

Advantageously, the material use to form the second member 25 may be one of plastic material especially resins, known to be use in dentistry. This second member 25-may be fastened on the first member by any appropriate technique well known and recognized is the art (e.g. gluing).

Advantageously, teeth are made with a usual material in the field of dentistry.

The housing 29 is obtained according to usual technics involving the use of a "matrix" identical to the shape of the infrastructure with the gingiva 9 and on which the infrastructure 1 is mounted and the first member 19 is cast within an appropriate mould. That technic is well known in the art and does not need to be explained in detail. Nevertheless, it must be noted that the "matrix" includes the "sliding surface" 33 and thereby forms, during the moulding, the sliding surface 39 in the housing 29 of the first member 19 to be obtained. Of course said housing 29 is formed by the presence of the connection bar 13 in the matrix. Furthermore, devices 51 may be mounted on the connection rod 13 so as to be surrounded by the molded metal or alloy and then locked in the hardened first member 19. The outer surface of the sleeve 53 may be provided at this end with protuberances.

Advantageously, the suprastructure 3 may be further provided with a lip support 79. It may be made of plastic material especially resins known to be used in dentistry. This lip support 79 allows to support the lip 81 of a person (see FIG. 5). The lip support 79 may be fastened on the first member by any appropriate techniques well known and recognised in the art (e.g. gluing). Preferably, the second member 25 and the lip support 79 are made in of single piece of material.

It is possible to use a teeth prosthesis "P" according to a method involving the following steps:

for mounting the suprastructure on the infrastructure, one only have to move both sliding surface one against the other and to fasten the rear ends of the member with the corresponding rear ends of the connection bar;

for removing the suprastructure from the infrastructure, one only have to unfasten the rear ends of the member from the corresponding rear ends of the connection bar and to move the sliding faces away from each other. More particularly, with the prosthesis "P" defined hereinabove the following steps may be carried out:

for mounting the suprastructure 3 on the infrastructure 1, one only have to grasp the fore part 21 of the suprastructure 3 and put sliding faces 33, 39 one against the other, to house each protuberance 61 of the connection bar 13 in a corresponding housing of the member 19 to thus co-axially align the longitudinal axis of each bore 59 of the connection bar 13 with the longitudinal axis of a corresponding sleeve 53, and then to push each pin 57 with his finger or his tongue to slid them in their respective cylindrical sleeve 53 and through a corresponding bore 61 of the connection bar 13;

for removing the suprastructure 3 from the infrastructure 1, one only have to introduce a fine pin 83 through the said bore 75 of the suprastructure 3 and push the pin 57 until it no longer face the lateral opening 53 of its corresponding cylindrical sleeve 53, to remove said fine pin 83 from said bore 75 and introduce it through the other bore 75 of the suprastructure 3 and push the pin 57 until it no longer face the lateral opening 5 of its corresponding cylindrical sleeve 53, and then to grasp the fore part 21 of the suprastructure 3 and remove both sliding faces 33, 39 from each other.

Preferably, when sliding faces are slid one against the other during the mounting of the suprastructure 3 on the infrastructure 1 or the removing of the suprastructure 3 from the infrastructure 1, said faces are moved substantially parallel. (i.e. thus the suprastructure 3 is moved with respect to the infrastructure 1 according to an angle substantially parallel with a plane containing said sliding surface 33).

Of course, the invention also relates to all variations that could be obvious to a man skilled in the art.

What is claimed is:

1. A teeth prosthesis for an upper maxilla, said prosthesis comprising an infrastructure, a suprastructure and means for a removable attachment of the suprastructure with the infrastructure;

said infrastructure comprising:
at least three implants, each implant having opposite ends, one end of each implant being anchored in the bone of the upper maxilla while the opposite end is sticking out of the gingiva and defines a head to said implant,
one connection bar having a fore part and two opposite rear ends, said bar being shaped and sized to be substantially facing the gingiva of the upper maxilla,
means for removably fastening the connection bar with and against each head of said implants;

said suprastructure comprising:
a first member made of cast metal or alloy, and having a fore part and two rear ends, having an intrados provided with an opening giving access to a housing provided in the member, said housing being of such size and depth to allow the housing of the connection bar therein,
a second member immovably attached with the first member, said first and second members defining together a saddle, and
a set of teeth immovably attached with the first member and the second member;

said means for a removable attachment of the suprastructure the infrastructure comprising:
two first fastening means that are respectively immovably attached with a corresponding rear end of the member for removably attaching them with corresponding ends of the connection bar,
a second fastening means comprising a first sliding face provided on the fore part of the connection bar and inclined toward the rear of said connection bar, a lower part of said face forming with a bottom face of said connection bar an edge projecting ahead the connection bar, and a second sliding face provided on a fore wall of the housing of the first member, said sliding faces, when the first and second fastening means are attached with the connection bar, cooperating together to lock the fore part of the member against the fore part of the connection bar and press a fore part of the saddle against the corresponding portion of gingiva of the upper maxilla.

2. A teeth prosthesis according to claim 1, wherein said first fastening means respectively comprising:
a device that is immovably attached with a corresponding end of the member, said device comprising a cylindrical sleeve provided with a lateral opening, and a pin slidably mounted inside the sleeve and movable between two distinct positions, a first distinct position being defined when the pin is not facing the lateral opening and a second distinct position being defined when the pin is facing the lateral opening,
a bore provided in a small protuberance near corresponding end of the connection bar, said protuberance being shaped and sized to be housed in a corresponding cylindrical sleeve through the lateral opening of said cylindrical sleeve and co-axial with a longitudinal axis of the cylindrical sleeve, said bore being removably engageable by said pin.

3. A teeth prosthesis according to claim 2, wherein the cylindrical sleeve and the pin are both of such size to be completely housed between an inner and an outer lateral walls of the suprastructure, when the pin is slid completely inside the cylindrical sleeve, and wherein a portion of the pin projects from the corresponding inner wall of the suprastructure when the pin is slid to be not facing the lateral opening of the cylindrical sleeve, a first bore co-axial with the longitudinal axis of the pin being provided in the corresponding inner wall of the suprastructure to allow the passage of the pin therethrough and a second bore of size smaller than a diameter of the pin and co-axial with the longitudinal axis of said pin being provided in the corresponding outer wall of the suprastructure, said second bore allowing a small tool to push the pin from a distinct position where it faces the lateral opening of the cylindrical sleeve toward the other distinct position where said pin does not face said lateral opening.

4. A teeth prosthesis according to claim 3, wherein at least four implants are provided.

5. A teeth prosthesis according to claim 4, wherein five or six implants are provided.

6. A teeth prosthesis according to claim 3, wherein four implants are provided and wherein each implant is of the type made with titanium.

7. A teeth prosthesis according to claim 3, wherein the suprastructure is further provided with a lip support.

8. A method of use of a teeth prosthesis as defined in claim 3, wherein:
for mounting the suprastructure on the infrastructure, one only has to grasp the fore part of the suprastructure and put sliding faces one against the other, to house each protuberance of the connection bar in a corresponding housing of the first member to thus co-axially align the longitudinal axis of each bore of the connection bar with the longitudinal axis of a corresponding sleeve, and then to push each pin with one of his finger or his tongue to slid them in their respective cylindrical sleeve and through a corresponding bore of the connection bar;
for removing the suprastructure from the infrastructure, one only have to introduce a fine pin through the said second bore of the suprastructure and push the pin until it no longer faces the lateral opening of its corresponding cylindrical sleeve, to remove said fine pin from said first of said second bore and introduce it through a second of said second bore of the suprastructure and push the pin until it no longer face the lateral opening of its corresponding cylindrical sleeve, and then to grasp the fore part of the suprastructure and remove both sliding faces from each other.

9. A method according to claim 8, wherein when sliding faces are slid one against the other during the mounting of the suprastructure on the infrastructure or the removing of the suprastructure from the infrastructure, said faces are moved substantially parallel.

10. A method of use of a teeth prosthesis as defined in claim 1, wherein:

for mounting the suprastructure on the infrastructure, one only has to move both sliding surface one against the other and to fasten the rear ends of the member with the corresponding rear ends of the connection bar;

for removing the suprastructure from the infrastructure, one only have to unfasten the rear ends of the member from the corresponding rear ends of the connection bar and to move the sliding faces away from each other.

* * * * *